United States Patent [19]
Anderson et al.

[11] Patent Number: 6,063,054
[45] Date of Patent: May 16, 2000

[54] INJECTOR PUMP

[75] Inventors: Mark L. Anderson, 303 S. MacKay Ave., Spring Valley, Wis. 54767; Adrian Currey, Holt, United Kingdom

[73] Assignee: Mark L. Anderson, Spring Valley, Wis.

[21] Appl. No.: 09/078,090

[22] Filed: May 13, 1998

[51] Int. Cl.$^7$ .................................................. A61M 5/307
[52] U.S. Cl. ................................. 604/70; 68/141; 68/143; 68/152
[58] Field of Search ..................................... 604/141, 143, 604/151, 152, 68, 69, 70

[56] References Cited

U.S. PATENT DOCUMENTS

| | | | |
|---|---|---|---|
| 3,051,173 | 8/1962 | Johnson et al. | 604/152 |
| 3,353,537 | 11/1967 | Knox et al. | |
| 3,515,130 | 6/1970 | Tsujino | 604/70 |
| 3,727,614 | 4/1973 | Kniazuk | 604/152 X |
| 4,596,556 | 6/1986 | Morrow et al. | |
| 4,680,027 | 7/1987 | Parsons et al. | |
| 4,913,699 | 4/1990 | Parsons | |
| 5,632,730 | 5/1997 | Reinert | |

FOREIGN PATENT DOCUMENTS

2 288 539   4/1998   United Kingdom.

*Primary Examiner*—Jeffrey A. Smith
*Attorney, Agent, or Firm*—Skinner and Associates

[57] ABSTRACT

A pump, comprising an inlet portion having an ingress channel, an outlet portion having an egress channel, a firing portion, and a manifold having a passage in fluid communication with the ingress channel, the egress channel, and the chamber. The firing portion includes a firing cylinder and a firing piston. The firing piston is capable of performing compression strokes and expansion strokes within the firing cylinder. The firing cylinder forms a chamber in which fluid is drawn during an expansion stroke. A high-pressure actuation device drives the firing piston during the compression stroke to expel a high-pressure jet of fluid from the egress channel. If an injector device is held proximate to flesh, the jet of fluid has sufficient pressure to hypodermically inject the fluid without a needle. The inlet portion, outlet portion, and firing portion of the pump can be rearranged on the manifold to conform to the design requirements for a variety of slap injectors.

15 Claims, 6 Drawing Sheets

INJECTOR PUMP

BACKGROUND OF THE INVENTION

1. Field of the Invention

The invention relates to apparatus and methods for administering measured doses and particularly, but not exclusively, to apparatus and methods for automatically, accurately and quickly dispensing and administering measured liquid volumes from injectors. The invention has particular utility for veterinary purposes such as the needleless, hypodermic dosing of animals with liquid medicaments. The invention is especially useful in slap injectors designed to dose animals of free range. However, it will be appreciated from the following description that the invention is not limited to such applications and may be used for many other purposes where it is necessary to quickly and accurately dispense repeated, measured volumes of a liquid.

2. Background Information

The state of the art generally includes various devices and methods for automatically dispensing and administering measured volumes of fluid into animals. For example, a common device is a hand-held injection gun that has a projecting needle and a trigger mechanism. The needle is introduced into the body of the animal and the trigger mechanism is squeezed to actuate a syringe-like device that delivers the injectate along the hollow needle and into the animal. While such injection guns are effective where the animal is closely restrained and comparatively still, they may be difficult to operate with comparatively unrestrained animals or with animals of free range because it is difficult to synchronize the operation of the trigger with the insertion of the needle in the animal. In order to overcome this problem, slap injectors have been designed to be slapped or prodded against the body of an animal. The impact of the device against the animal automatically projects a hollow needle through the animal's skin and triggers a discharge of a measured dose of injectate through the needle. The slap injector may have a straight-on design wherein the needle and handle are aligned and the slap injector is thrust into the animal to trigger the discharge, or the slap injector may have an angled design wherein the needle and handle form an angle, preferably a 90° angle, and the slap injector is swung in a hammer-like motion into contact with the animal.

An example of an angled slap injector is disclosed in British Patent No. 2288539 entitled Slap Injector, and is hereby incorporated by reference. The slap injector generally comprises a handle, a body part, a syringe device, operating means, a trigger device, and actuating means. The body part is mounted to one end of the handle. A hollow needle projects from the body part. The actuation means is mounted on the body part and actuates the trigger device, which upon engagement with an animal, controls the operating means. In use, the handle is swung so that the actuating means engages the body of the animal being injected and is displaced relative to the body part of the device as the needle passes into the body of the animal. The displaced actuating means actuates the trigger device, and the actuated trigger device permits the operating means to discharge the syringe device. Preferably return means return the actuating means to its initial position relative to the body part after the syringe device is discharged and automatically withdraws the needle from the body of the animal. The return means may comprise first spring means arranged to oppose the initial movement of the actuating means relative to the body part and to return the actuating means to its initial position after the discharge of the syringe device. The actuating means may include a slap plate extending transversely to the hollow needle. The needle projects through an aperture in the slap plate as it is displaced relative to the body part. The apertured slap plate guides and supports the needle as it is inserted into the animal, thus reducing the risk of bending the needle. The outer surface of the slap plate is preferably convexly curved with the needle aperture located at the lowermost point of the curve. This design allows the fill length of the needle to pass into the animal even if the device is not applied perfectly squarely to the animal's hide. The actuating means may also include a peripheral wall which surrounds and shields the needle when the actuating means is in its initial position. The operating means for discharging the syringe device may comprise an operating element and second spring means for displacing the operating element from a cocked position in which the spring means is stressed to an extended position in which the spring means is released. The operating element is held in the cocked position by the trigger device, and is operatively coupled to discharge the syringe device as it moves to the extended position. Preferably the operating element and second spring means extend longitudinally with respect to the handle of the injecting device.

Slap injectors are generally effective, but may encounter problems while dosing an animal. One potential problem is that the needle may bend and harm the animal. Another problem is that inaccurate or inconsistent dosages may be delivered because the slap injector was not in operational contact with the animal for a period of time long enough to fully discharge the desired dose into the animal.

Applicants' invention provides an injector pump which can be incorporated into a new and improved design of a slap injector. Specifically, applicants' invention is a high-pressure pump of flexible design that quickly and repeatably delivers an accurate measured volume under high pressure into an animal with or without a needle.

BRIEF SUMMARY OF THE INVENTION

The present invention provides an injector pump which generally comprises an inlet portion, an outlet portion, a firing portion and a manifold. The inlet portion has an ingress channel, the outlet portion has an egress channel, and the firing portion has a chamber, all of which are in fluid communication with a passage in the manifold. A firing piston slides within a firing cylinder in the firing portion and forms the chamber. The cross sectional area of the firing cylinder is relatively small. A high-pressure actuation device applies pressure to the piston, and because of the small area of the piston head, quickly drives the piston through its compression stroke and expels fluid at a great speed from the pump. One-way valves are positioned within the ingress channel and the egress channel to control fluid flow within the pump. Fluid is drawn from the inlet channel and into the chamber during an expansion stroke of the piston, and fluid is expelled from the chamber and through the egress channel and a nozzle during a compression stroke of the piston.

In one embodiment, the injector pump further includes a needle holder screwed onto the nozzle of the outlet portion. A hollow needle may be screwed into the needle holder so that the hollow needle is in fluid communication with the egress channel.

In another embodiment of the injector pump, the manifold has similarly-dimensioned interior threaded apertures and the inlet portion and the outlet portion have similarly dimensioned exterior threaded necks. The inlet portion and outlet portion may be unscrewed and removed from the manifold, and they may exchange positions with each other as they are re-screwed onto the manifold to create an injector pump having a different configuration for a different slap injector design. Additionally, the firing portion may be designed with a similarly-dimensioned exterior threaded neck so that the firing portion could exchange positions with the inlet portion or the outlet portion to provide additional configurations.

Significant features of the invention include the flexible design of a high-pressure pump that can be incorporated into various existing designs of slap injectors. The components of the injector pump are easily exchanged with each other on the manifold to accommodate a variety of slap injectors. Furthermore, the injector pump is designed as a high-pressure pump. A high-pressure actuation device quickly drives the piston through its compression stroke to expel the measured volume from the chamber, and because of the small cross sectional area of the firing cylinder and the small diameter of the egress channel, a fluid stream is expelled from the nozzle with sufficient force to provide an accurate, needleless, hypodermic dose of an animal.

The features, benefits and objects of this invention will become clear to those skilled in the art by reference to the following description, claims and drawings.

DETAILED DESCRIPTION

Examples of preferred embodiments of the present invention are illustrated and generally indicated by the reference numeral 10 in FIGS. 1–5. The injector pump 10 is described below first in terms of its major structural elements and then in terms of its secondary structural and/or functional elements which cooperate to quickly and repeatably deliver an accurate dose under high pressure. The injector pump 10 generally comprises an inlet portion 12, an outlet portion 14, a firing portion 16, and a manifold 18. The inlet portion 12, the outlet portion 14, the firing portion 16 and the manifold 18 all have passages that are in fluid communication with each other.

FIGS. 1–4 illustrate several embodiments of the injector pump 10 having different arrangements of these components. The exploded view of FIG. 5 and the cut away views of FIGS. 6a–6c generally illustrate the design of these components. The inlet portion 12 has an ingress channel 20, a stem 22 for attaching a hose or other fluid conduit from a fluid source, and an exterior threaded neck 24. The outlet portion 14 has an egress channel 26 and a threaded neck 28. The firing portion 16 has a firing piston 30 that slides within a firing cylinder 32 and forms a chamber 34 within the cylinder 32. The manifold 18 has a passage 35 that provides fluid communication between the ingress channel 20, the egress channel 26, and the chamber 34.

A first one-way valve 36, such as a ball-check valve, is positioned within the ingress channel 20 and a second one-way valve 38 is positioned within the egress channel 26. The valves 36 and 38 control or govern the fluid flow within the injector pump 10. Fluid flows from the ingress channel 20 into the chamber 34 during an expansion stroke of the piston 30 and flows from the chamber 34 through the egress channel 26 during a compression stroke of the piston 30.

Figure 6A:
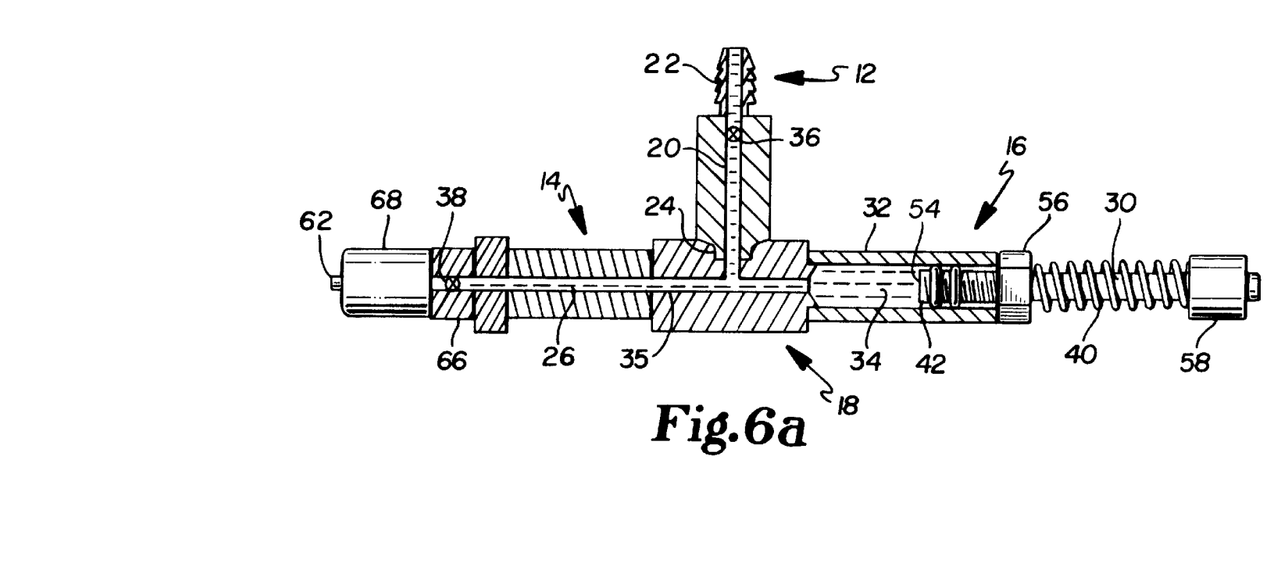
FIG. 6a is a partial cross sectional view of the injector pump of FIG. 1 primed with fluid in the chamber.
Figure 6B:
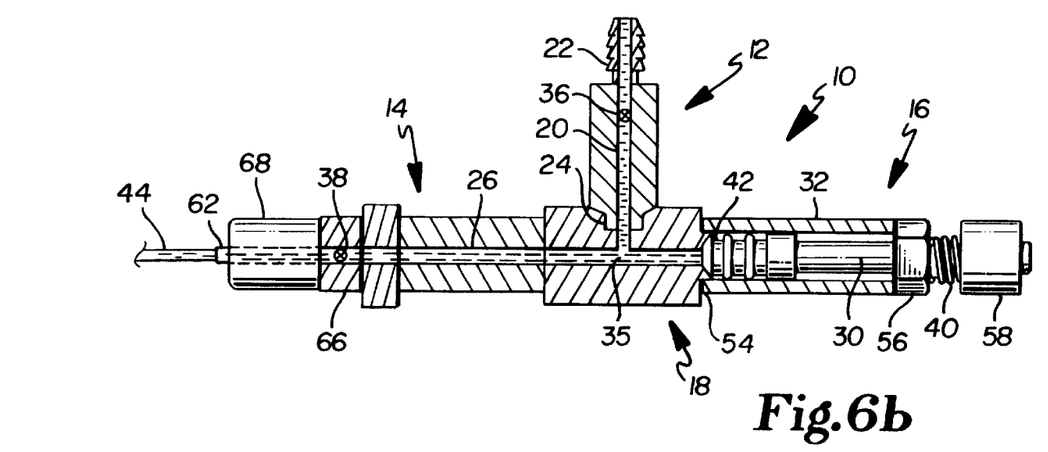
FIG. 6b is a partial cross sectional view of the injector pump of FIG. 1 after the piston has been driven through its compression stroke and has expelled fluid from the chamber and through the outlet portion.
Figure 6C:
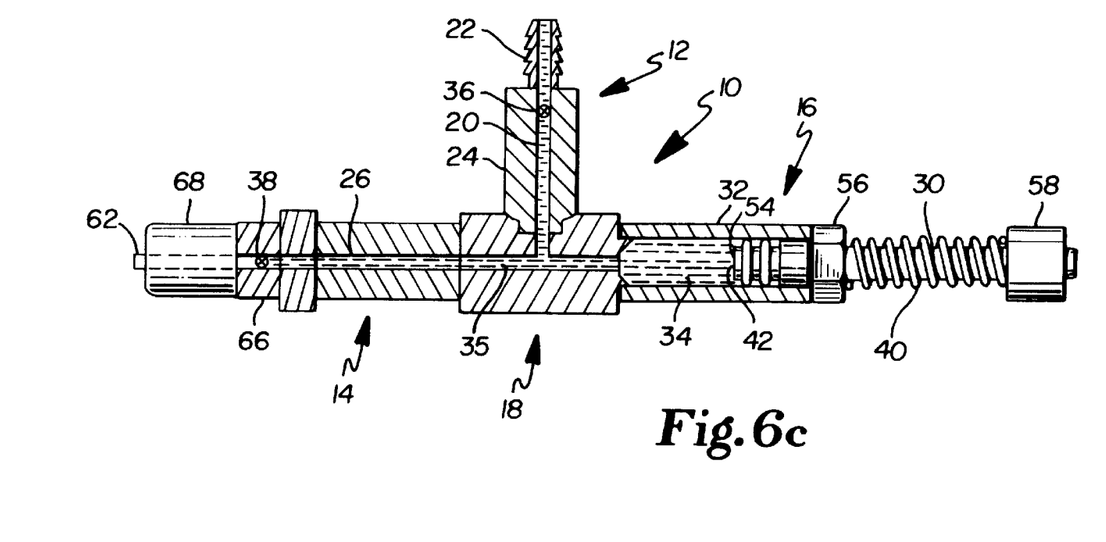
FIG. 6c is a partial cross sectional view of the injector pump of FIG. 1 after the piston has drawn fluid into the chamber.

FIGS. 6a–6c illustrate the injector pump 10 prior to the compression stroke, after the compression stroke, and after the expansion stroke. These figures show a pre-primed device. The ingress channel 20, egress channel 26, and passage 35 are preferably constructed as small as operationally possible to reduce the amount of the air present within these passages during the priming of the pump 10. Furthermore, the channels 20 and 26, the passage 35, and the chamber 34 are precision machined to accurately deliver a desired volume of fluid corresponding to the volume of the chamber 34, which is defined by the interior diameter of the cylinder 32 and the stroke distance of the piston 30.

The firing piston 30 is driven by a high-pressure actuation device to quickly drive the piston 30 through its compression stroke. The high-pressure actuation device may be a powerful spring 40 as shown in the figures, a compressed gas cartridge, a compressed air line, or other means for providing sufficient pressure to quickly fire or drive the piston through its entire compression stroke. The small cross sectional area of the firing cylinder 32 assists with the quick compression stroke motion. As shown in FIGS. 6a–6c, the spring 40 applies pressure the piston 30 and expels a high-pressure jet 44 of fluid from the pump 10.

Figure 1:
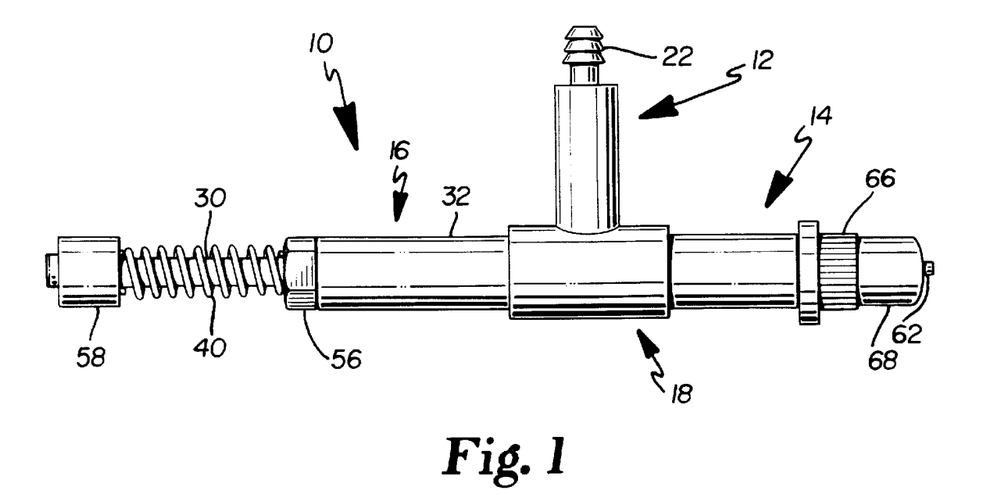
FIG. 1 is a planar view of an embodiment of the injector pump of the present invention.

Each of the portions 12, 14 and 16 may be integrally formed with the manifold 18. However, as shown in the exploded view of FIG. 5, the manifold 18 preferably has apertures 46 with interior threads. These interior threaded apertures 46 preferably have similar dimensions, including the diameter, the thread pitch, and the minimum and maximum thread diameters. FIG. 5 shows the inlet portion 12 and the outlet portion 14 with similarly-dimensioned exterior threaded necks 24 and 28. These similar dimensions include the diameter, the thread pitch, and the minimum and maximum thread diameters. The firing portion 16 is shown in this embodiment as being integrally formed with the manifold 18. Because of their similar design and dimensions, each neck 48 can be screwed into each of the apertures 46 in the manifold 18. Therefore, the inlet portion 12 and outlet portion 14 may exchange positions as seen in FIGS. 1 and 3. The firing portion 16 may also be formed with a similarly dimensioned exterior threaded neck. Thus, the injector pump 10 can form numerous configurations using prefabricated components. FIGS. 1–4 provide examples of these configurations. Although threaded couplings are shown in the preferred embodiment, it is anticipated that other couplings or connectors could be used to attach the components to the manifold 18 within the teachings of this invention.

Figure 4:
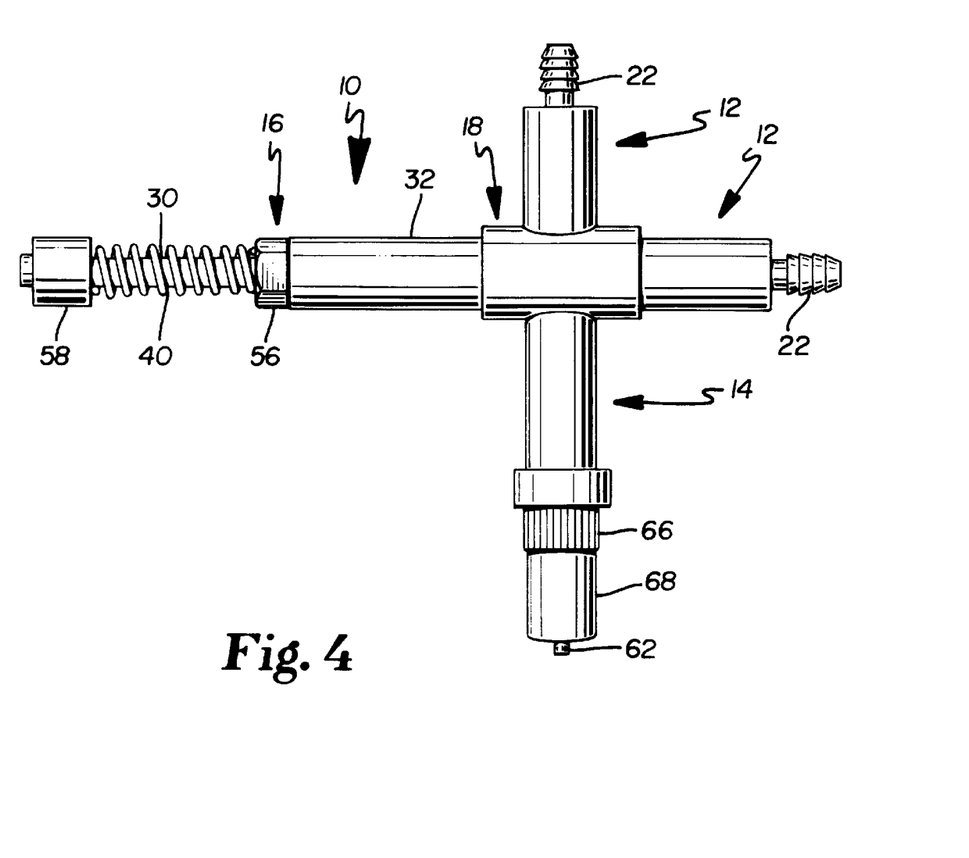
FIG. 4 is a planar view of another embodiment of the injector pump of FIG. 1.
Figure 5:
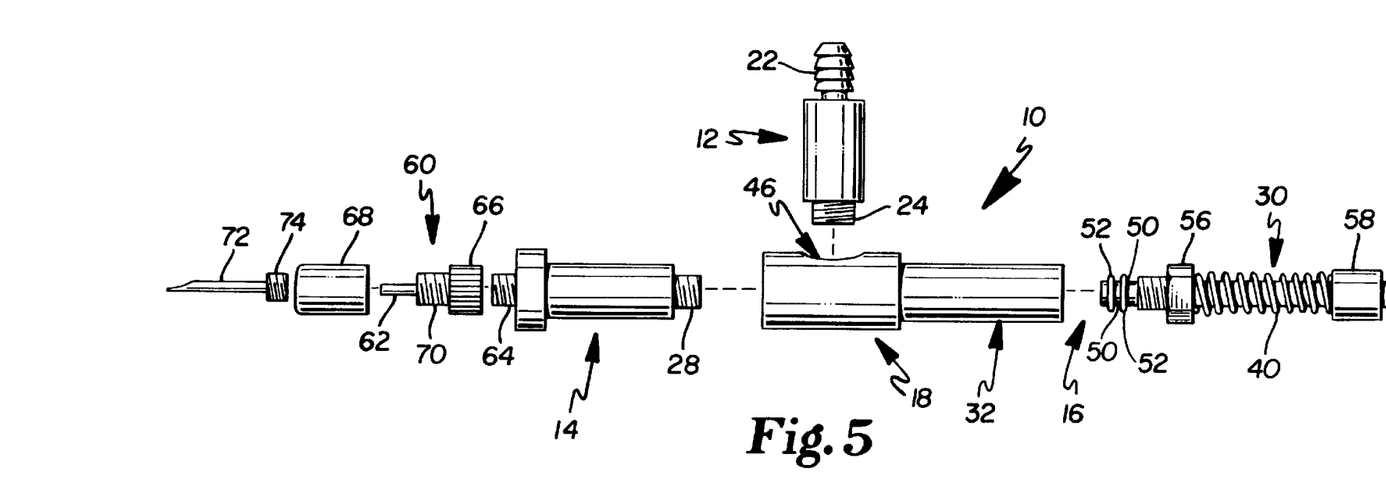
FIG. 5 is a partially exploded, planar view of the injector pump of FIG. 1.

FIG. 4 shows a manifold 18 adapted to accommodate a firing portion 16, an outlet portion 14, and two inlet portions 12. The inlet portions 12 allows fluid to be drawn from two separate fluid sources and mixed within the injector pump 10. If the manifold 18 is designed with four threaded apertures 46 and if only one inlet portion 12 is required, a threaded plug (not shown) designed to adequately enclose the passage 35 may be screwed into the fourth aperture in the manifold 18.

The piston head 42 is designed to quickly, effectively, and efficiently displace fluid from the chamber 34 when the high-pressure actuation device forcefully drives the piston 30 through its compression stroke and expels fluid through the egress channel 26. As shown most clearly in FIG. 5, the piston head 42 preferably has two grooves 50 with an annular, rubber-like ring 52 seated within each groove 50. The piston head 42 further has a beveled leading edge 54. The overall design of the piston head 42 and the smooth interior of the cylinder 32 provide the piston 30 with a desired smooth, low-friction motion within the cylinder 32.

As shown in FIGS. 1–5, the firing portion 16 may also include a nut-like sleeve 56 screwed into a threaded end of the cylinder 32. The piston 30 extends through and has a low-friction, precision fit within the sleeve 56. The sleeve effectively captures the piston head 42 within the cylinder 32 and guides the piston 30 during the compression and expansion strokes. FIGS. 1–5 also show a cap 58 screwed onto the end of the piston 30. The spring 40 is effectively captured between the cap 58 and the sleeve 56.

The outlet portion 14 has a nozzle 60 with an outlet 62 in fluid communication with the egress channel 26. A high-pressure jet 44 of fluid is expelled from the outlet 62 with sufficient force to provide a needleless, hypodermic injection into the flesh of an animal. Referring to FIG. 5, the nozzle 60 has an interior threaded surface and the outlet portion 14 has a second exterior threaded surface 64 on which the nozzle 60 is screwed. The nozzle 60 has a knurled surface 66 that assists with the manipulation of the nozzle 60 when it is being screwed on and off of the outlet portion 14. A needle holder 68 may be screwed onto an exterior threaded surface 70 on the nozzle 60 and a hollow needle 72 having exterior threads 74 may be screwed into the distal end of the needle holder 68. A mounted hollow needle 72 is in fluid communication with the egress channel 26 and may be used in the hypodermic dosing of animals.

The injector pump 10 is preferably fabricated from a durable plastic material and is designed to withstand the repetitive force associated with the high-pressure actuation device. The injector pump 10 is precision machined to provide small passages 20, 26 and 35, and to provide a predetermined volume within the chamber 35. This precision allows the pump 10 to repeatably and accurately expel predetermined volumes of fluid from the outlet 62. The flexible design of the injector pump 10 provides significant manufacturing benefits. The same components can be used for a variety of pump design configurations allowing the manufacturer to realize larger economies of scale.

Figure 2:
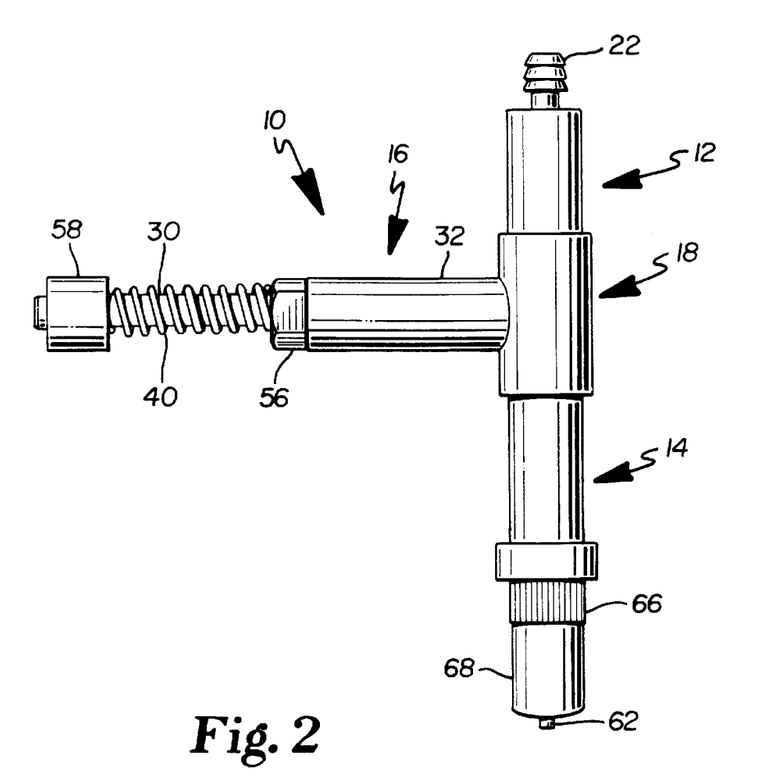
FIG. 2 is a planar view of another embodiment of the injector pump of FIG. 1.
Figure 3:
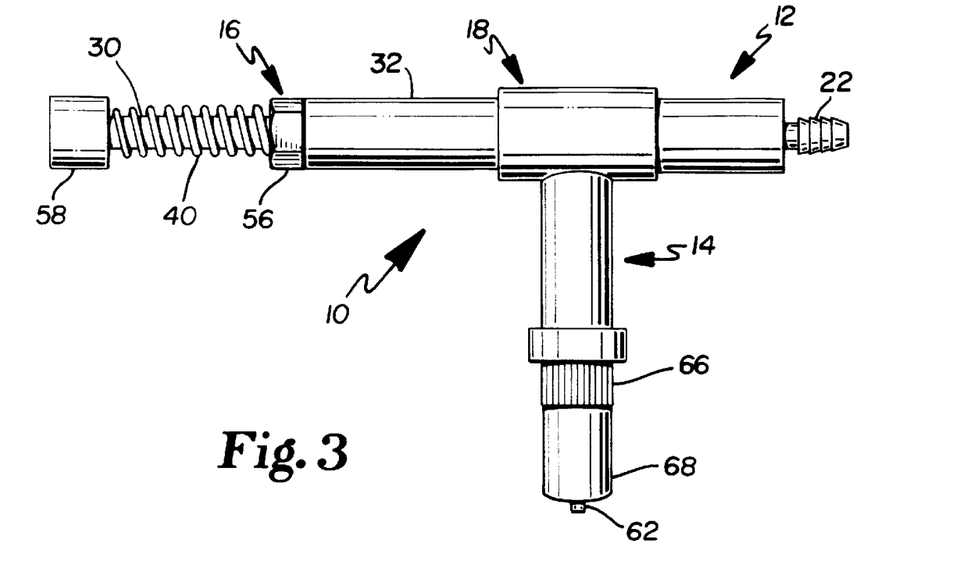
FIG. 3 is a planar view of another embodiment of the injector pump of FIG. 1.
Figure 7:
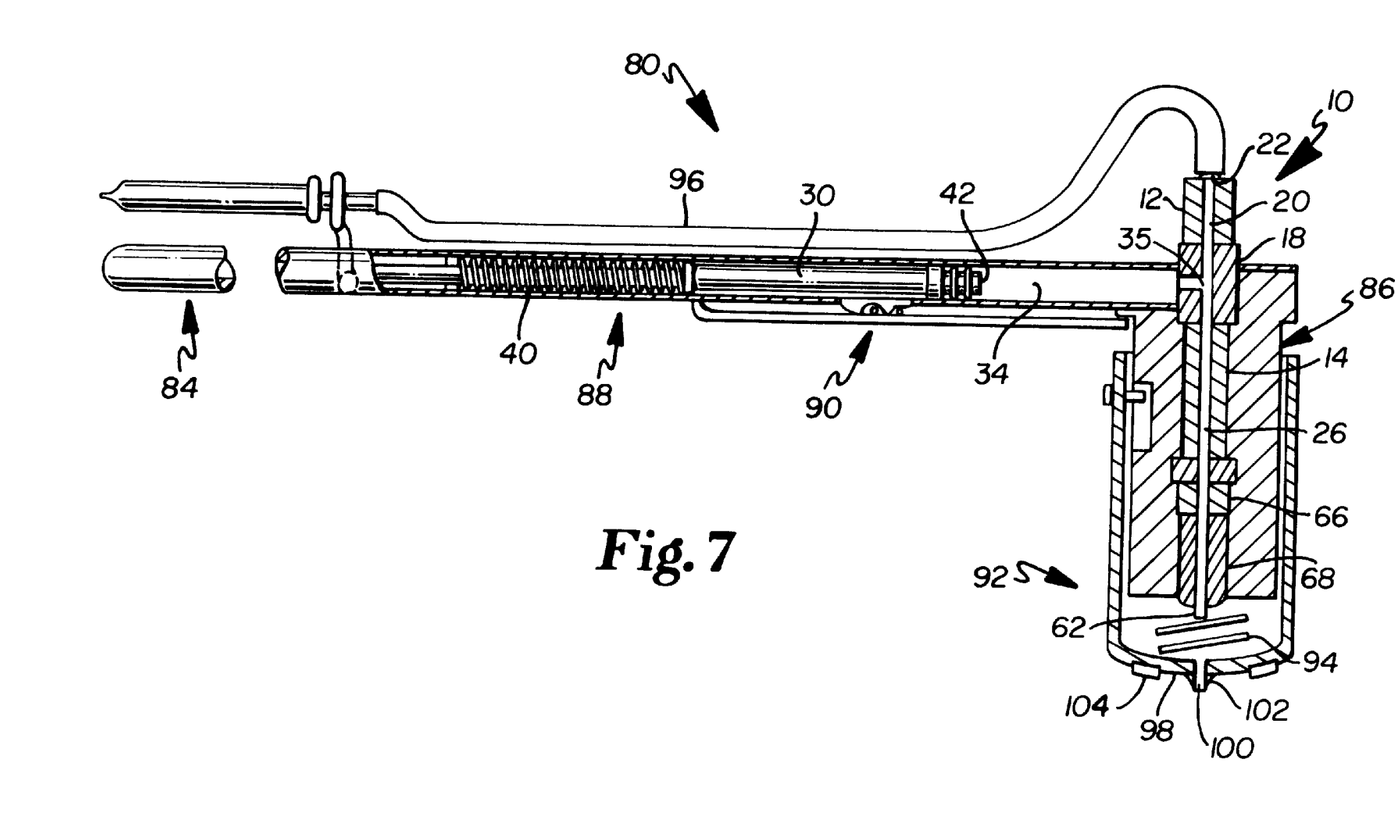
FIG. 7 is a planar view, partially in cross section, of an embodiment of the injector pump used in an angled design of a slap injector.
Figure 8:
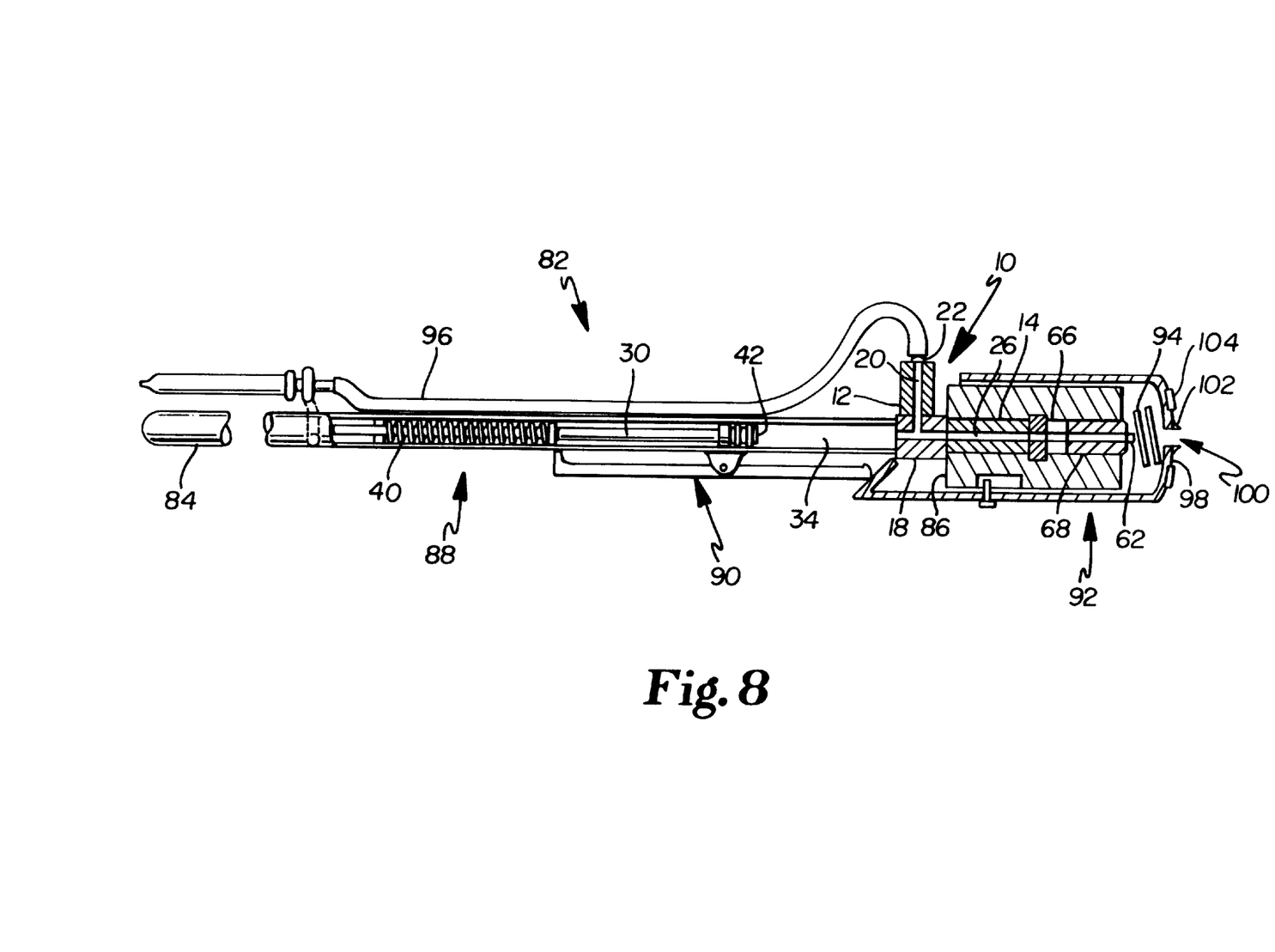
FIG. 8 is a planar view, partially in cross section, of an embodiment of the injector pump used in a straight-on design of a slap injector.

FIG. 7 shows an angled slap injector 80, illustrated at approximately 90 degrees, incorporating an embodiment of the injector pump 10 similar to that shown in FIG. 2. FIG. 8 shows a straight-on slap injector 82 incorporating an embodiment of the injector pump 10 similar to that shown in FIG. 1. The figures approximate the basic structural layout of two slap injector designs to illustrate the flexible design of the injector pump 10. In both embodiments 80 and 82, the slap injector generally comprises a handle 84, a body part 86, the injector pump 10, operating means 88, a latch or trigger device 90, and triggering or actuating means 92.

A fluid conduit 96 provides fluid communication between a fluid source and the injector pump 10. The body part 86 is mounted to one end of the handle 84. The actuation means 92 is mounted on the body part 86 and, upon contacting an animal, triggers or actuates the trigger device 90. The trigger device 90 is designed to latch and release the operating means 88.

In operation, the handle 84 is swung so that the actuating means 92 contacts the animal and is displaced relative to the body part 86. The displaced actuating means 92 functions as a triggering mechanism to actuate the trigger device 90, which is functioning as a latch device with respect to the operating means 88. The actuated trigger device 90 releases the operating means 88. The released operating means 88 fires or drives the piston 30 through a compression stroke and expels a high-pressure jet of fluid through the egress channel 26 and the outlet 60. The operating means 88 for driving the piston 30 preferably comprises a high-pressure actuation device such as a compressed gas capsule, a compressed air line, or a strong spring 40. Preferably return means, such as a spring 94, returns the actuating means 92 to its initial position relative to the body part 86 after fluid has been expelled from the outlet 60.

The figures show the operating means 88, including the spring 40 and a coupling between the spring 40 and piston 30, in a cocked position in which the spring 40 is stressed. The trigger device 90 latches the operating means in the cocked position. Unlatching the trigger device 90 from the operating means 88 permits the operating means 88 to move to an uncocked position by allowing the spring 40 to expand. Actuating the trigger device 90 allows the spring 40 to drive the piston 30 through its compression stroke to expel fluid through the egress channel 26. Preferably the operating means 88 and spring 40 extend longitudinally with respect to the handle 84 of either embodiment of the slap injector 80 and 82.

The actuating means 92 may contain a slap plate 98 designed to contact the animal. The slap plate 98 has an aperture 100 through which the high-pressure jet of fluid is expelled and through which the removable needle 72 may extend. FIGS. 7 and 8 show small barbs 102 extending from the slap plate 98 proximate to the aperture 100. The barbs 102 facilitate a needless hypodermic injection by breaking the tough skin on animals allowing the high-pressure jet to effectively and consistently penetrate into the muscular tissue. The figures also show a marking element 104 positioned on the slap plate 98. The marking element 104 contains an ink-like substance that leaves a mark on the skin of the animal upon contact. The marking element 104 is therefore useful to identify whether an animal has been treated and to identify the location of the treatment.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function it is intended that such claim be construed to cover the corresponding structure, material, or acts described in the specification and equivalents thereof, including both structural equivalents and equivalent structures.

What is claimed is:

1. A pump, comprising:
   (a) an inlet portion having an ingress channel in fluid communication with a fluid source, said inlet portion having an inlet portion connector;
   (b) an outlet portion having an egress channel, said outlet portion having an outlet portion connector similar in design and dimensions to said inlet portion connector;
   (c) a firing portion including a firing cylinder and a firing piston, said firing piston being adapted for performing compression strokes and expansion strokes within said firing cylinder, said firing cylinder forming a chamber;
   (d) a manifold having at least two connectors adapted for coupling with either said inlet portion connector or said outlet portion connector, wherein said inlet portion and said outlet portion are interchangeable and provide said pump with at least a first and a second configuration, said firing piston moving in a direction aligned with said egress channel in said first configuration and moving in a direction not aligned with said egress channel in said second configuration, said manifold having a passage in fluid communication with said ingress channel, said egress channel, and said chamber;
   (e) a one-way inlet valve positioned within said ingress channel, said inlet valve permitting fluid to flow through said ingress channel, through said passage, and into said chamber during an expansion stroke of said firing piston and preventing fluid from flowing from said passage through said ingress channel during a compression stroke of said firing piston; and
   (f) a one-way outlet valve positioned within said egress channel, said outlet valve permitting fluid to flow from said passage through said egress channel and said outlet during a compression stroke of said firing piston and preventing fluid from flowing from said egress channel into said passage during an expansion stroke of said firing piston.

2. The pump of claim 1, wherein said inlet portion includes a stem, said ingress channel extending through said stem.

3. The pump of claim 1, wherein said outlet portion includes a nozzle, said egress channel extending through said nozzle and terminating at an outlet.

4. The pump of claim 3, wherein said nozzle has an exterior threaded surface, said outlet portion further including a needle holder, said needle holder having an interior nozzle threaded surface cooperating with said exterior threaded surface of said nozzle, said needle holder further having an interior needle threaded surface, whereby a hollow needle may be screwed into said interior needle threaded surface providing fluid communication between said outlet and said hollow needle.

5. The pump of claim 1, wherein said at least two connectors of said manifold include at least two threaded apertures and both said inlet portion connector and said outlet portion connector include a threaded neck, said necks being capable of screwing into either of said at least two threaded apertures.

6. The pump of claim 1, wherein a first end of said firing cylinder has a threaded first end, said firing portion further including a threaded sleeve, said firing piston including a piston head attached to a piston shaft, said piston shaft extending through said sleeve, said sleeve being capable of screwing onto said threaded first end of said firing cylinder and enclosing said piston head within said firing cylinder.

7. The pump of claim 1, wherein said firing piston includes a piston head attached to a piston shaft, said piston head having at least one circumferencial groove and further having at least one annular ring seated within said at least one circumferencial groove.

8. The pump of claim 1, wherein said firing piston moves in a direction aligned with said egress channel.

9. The pump of claim 1, wherein said firing piston moves in a direction at an approximately 90 degree angle with respect to said egress channel in the second configuration.

10. A high-pressure injector pump capable of being incorporated within either a straight-on or angled design of a slap injector dispenser, said dispenser administering quick, accurate doses in livestock, said pump comprising:
    (a) an inlet portion having an ingress channel in fluid communication with a fluid source, said inlet portion having a threaded neck;
    (b) an outlet portion having an egress channel, said outlet portion having a threaded neck similar in design and dimension to said threaded neck of said inlet portion;
    (c) a firing portion including a firing cylinder and a firing piston, said firing piston being adapted for performing compression strokes and expansion strokes within said firing cylinder, said firing cylinder forming a chamber, said firing piston including a piston head attached to a piston shaft, said piston head having at least one circumferencial groove and further having at least one annular ring seated within said at least one circumferencial groove, said firing piston being driven during said compression stroke by a high-pressure actuation device;
    (d) a manifold having at least two threaded apertures adapted to receive either of said threaded necks, wherein said inlet portion and said outlet portion are interchangeable and provide at least a first and a second configuration, said firing piston moving in a direction aligned with said egress channel in said first configuration as used within a straight-on slap injector dispenser and moving in a direction not aligned with said egress channel in said second configuration as used in an angled slap injector dispenser, said manifold having a passage in fluid communication with said ingress channel, said egress channel, and said chamber;
    (e) a one-way inlet valve positioned within said ingress channel, said inlet valve permitting fluid to flow through said ingress channel, through said passage, and into said chamber during an expansion stroke of said firing piston and preventing fluid from flowing from said passage through said ingress channel during a compression stroke of said firing piston; and
    (f) a one-way outlet valve positioned within said egress channel, said outlet valve permitting fluid to flow from said passage through said egress channel and said outlet during a compression stroke of said firing piston and preventing fluid from flowing from said egress channel into said passage during an expansion stroke of said firing piston.

11. An injector apparatus, comprising:
    (a) a handle enabling a user to manipulate said apparatus;
    (b) a high-pressure injector pump, including:
        (1) an inlet portion having an ingress channel and an inlet portion connector;
        (2) an outlet portion having an egress channel, said outlet portion having an outlet portion connector similar in design and dimensions to said inlet portion connector;
        (3) a firing portion including a firing cylinder and a firing piston, said firing piston being adapted for performing compression strokes and expansion strokes within said firing cylinder, said firing cylinder forming a chamber;

(4) a manifold having at least two connectors adapted for coupling with either said inlet portion connector or said outlet portion connector, wherein said inlet portion and said outlet portion are interchangeable and provide said pump with at least a first and a second configuration, said firing piston moving in a direction aligned with said egress channel in said first configuration and moving in a direction not aligned with said egress channel in said second configuration, said manifold having a passage in fluid communication with said ingress channel, said egress channel and said chamber;

(5) a one-way inlet valve positioned within said ingress channel, said inlet valve permitting fluid to flow through said ingress channel, through said passage, and into said chamber during an expansion stroke of said firing piston and preventing fluid from flowing from said passage through said ingress channel during a compression stroke of said firing piston; and (6) a one-way outlet valve positioned within said egress channel, said outlet valve permitting fluid to flow from said passage through said egress channel and said outlet during a compression stroke of said firing piston and preventing fluid from flowing from said egress channel into said passage during an expansion stroke of said firing piston;

(c) a fluid conduit providing fluid communication between a fluid source and said ingress channel;

(d) a high-pressure actuation device operationally engaged with said firing piston, said firing piston having a cocked position and an uncocked position; and (e) a trigger mechanism for activating said high-pressure actuation device to move said firing piston from said cocked position to said uncocked position and expelling fluid from said egress channel.

12. The injector apparatus of claim 11, wherein said high-pressure actuation device is a spring.

13. The injector apparatus of claim 11, wherein said high-pressure actuation device is a source of compressed gas.

14. The injector apparatus of claim 11, further including a latch device, said latch device having a latch position where said latch device maintains said firing piston in said cocked position against pressure applied by said high-pressure actuation device, and further having a release position where said latch device releases said firing piston allowing pressure applied by said high-pressure actuation device to drive said compression stroke of said firing piston and move said firing piston to said uncocked position, said trigger device unlatching said latch device into said release position.

15. A slap injector apparatus, comprising:

(a) a handle enabling a user to manipulate said apparatus;

(b) a high-pressure injector pump, including:

(1) an inlet portion having an ingress channel and a threaded neck;

(2) an outlet portion having an egress channel, said outlet portion having a threaded neck similar in design and dimensions to said threaded neck of said inlet portion;

(3) a firing portion including a firing cylinder and a firing piston, said firing piston being adapted for performing compression strokes and expansion strokes within said firing cylinder, said firing cylinder forming a chamber;

(4) a manifold having at least two threaded apertures adapted to receive either of said threaded necks, wherein said inlet portion and said outlet portion are interchangeable and provide said pump with at least a first and a second configuration, said firing piston moving in a direction aligned with said egress channel in said first configuration and moving in a direction not aligned with said egress channel in said second configuration, said manifold having a passage in fluid communication with said ingress channel, said egress channel, and said chamber;

(5) a one-way inlet valve positioned within said ingress channel, said inlet valve permitting fluid to flow through said ingress channel, through said passage, and into said chamber during an expansion stroke of said firing piston and preventing fluid from flowing from said passage through said ingress channel during a compression stroke of said firing piston; and (6) a one-way outlet valve positioned within said egress channel, said outlet valve permitting fluid to flow from said passage through said egress channel and said outlet during a compression stroke of said firing piston and preventing fluid from flowing from said egress channel into said passage during an expansion stroke of said firing piston; and (c) a fluid conduit providing fluid communication between a fluid source and said stem;

(d) a high-pressure actuation device operationally engaged with said firing piston, said firing piston having a cocked position and an uncocked position; and (e) a latch device having a latch position where said latch device maintains said firing piston in said cocked position against pressure applied by said high-pressure actuation device, and further having a release position where said latch device releases said firing piston allowing pressure applied by said high-pressure actuation device to drive said compression stroke of said firing piston and move said firing piston to said uncocked position; and (f) a trigger mechanism for unlatching said latch device and activating said high-pressure actuation device to move said firing piston from said cocked position to said uncocked position after said apparatus has effectively contacted animal flesh, said fluid being expelled from said egress channel into said flesh upon releasing said firing piston.

* * * * *